(12) United States Patent
Blake

(10) Patent No.: US 8,608,799 B2
(45) Date of Patent: Dec. 17, 2013

(54) UMBRELLA-SHAPED ACCOMMODATING ARTIFICIAL OCULAR LENS (AAOL) DEVICE

(75) Inventor: Larry W. Blake, Coto de Caza, CA (US)

(73) Assignee: Tekia, Inc., Irvine, CA (US)

( * ) Notice: Subject to any disclaimer, the term of this patent is extended or adjusted under 35 U.S.C. 154(b) by 1079 days.

(21) Appl. No.: 11/656,959

(22) Filed: Jan. 24, 2007

(65) Prior Publication Data

US 2007/0106381 A1   May 10, 2007

(51) Int. Cl.
*A61F 2/16* (2006.01)

(52) U.S. Cl.
USPC .......... 623/6.37; 623/5.12; 623/5.14; 623/6.4

(58) Field of Classification Search
USPC ............ 623/4.1, 6.11, 6.18–6.22, 6.29, 623/6.37–6.5, 5.11–5.15
See application file for complete search history.

(56) References Cited

U.S. PATENT DOCUMENTS

| | | | | | |
|---|---|---|---|---|---|
| 4,253,199 | A | * | 3/1981 | Banko | 623/6.13 |
| 4,406,285 | A | * | 9/1983 | Villasenor et al. | 606/166 |
| 4,439,873 | A | * | 4/1984 | Poler | 623/6.4 |
| 4,808,181 | A | * | 2/1989 | Kelman | 623/6.43 |
| 5,192,319 | A | * | 3/1993 | Worst | 623/6.43 |
| 5,476,514 | A | * | 12/1995 | Cumming | 623/6.37 |
| 5,609,630 | A | * | 3/1997 | Crozafon | 623/6.43 |
| 6,660,035 | B1 | * | 12/2003 | Lang et al. | 623/6.37 |
| 7,455,691 | B2 | * | 11/2008 | Feingold et al. | 623/6.49 |
| 2006/0095127 | A1 | * | 5/2006 | Feingold et al. | 623/5.15 |
| 2006/0271178 | A1 | * | 11/2006 | Christie et al. | 623/5.11 |

* cited by examiner

*Primary Examiner* — Paul Prebilic
(74) *Attorney, Agent, or Firm* — Klima Law Offices; William L. Klima

(57) ABSTRACT

An accommodating artificial ocular lens (AAOL) device including a lens optic portion connected to a pleated lens haptic portion to provide accommodation of vision of the eye.

27 Claims, 5 Drawing Sheets

UMBRELLA-SHAPED ACCOMMODATING ARTIFICIAL OCULAR LENS (AAOL) DEVICE

FIELD OF THE INVENTION

The present invention is directed to an umbrella-shaped accommodating artificial ocular lens (AAOL) device. A preferred embodiment of the artificial accommodating ocular lens (AAOL) device according to the present invention is an accommodating intraocular lens (IOL) device for placement in the capsular bag to replace the natural crystalline lens to both correct vision and provide accommodation of vision of the eye.

BACKGROUND OF THE INVENTION

The concept of removing and replacing the natural crystalline lens of the eye, for example, that has become opaque (cataract) with an intraocular lens (IOL) implant in the capsular bag located in the eye has been around for many years. Typical intraocular lenses include three (3) piece intraocular lenses and accommodating designs having a lens optic portion supported by a pair of opposed loop haptic portions connected to the lens optic portion. Another version of intraocular lenses (IOLs) is the plate-type haptic IOL having a lens optic portion and a pair of opposed plate haptic portions extending and connected to the lens optic portion. Both of these types of conventional and accommodative attempted or designed intraocular lenses (IOLs) are used to replace a cataract or diseased natural crystalline lens, or in some instances even a clear natural lens, for correction or improvement of vision. These types of intraocular lenses are known to provide little to slight accommodation of the vision of the eye.

Some basic refractive accommodation of the eye is believed to occur by the natural crystalline lens changing its shape and/or size by forces (e.g. tension, compression) and/or pressures exerted on the natural crystalline to change or vary its power. Specifically, the natural crystalline lens is enclosed within the capsular bag of the posterior chamber of the eye. The zonules (ligaments) connecting the capsular bag to the ciliary muscle of the eye can apply forces on the capsular bag which in turn places forces on the natural crystalline lens, which can change the lenses shape to change its power, since the natural crystalline lens is soft and pliable and can be squeezed thinner by these forces. Further, direct forces or a differential of forces can be applied to the capsular bag by pressure differentials on the front side verses the back side of the capsular bag (e.g. increased pressure in a portion of the posterior chamber located behind the capsular bag), which forces tend to move the capsular bag and natural crystalline lens together as an accommodating unit forward and backward within the eye during accommodation. These forces and/or pressures exerted in the eye will result in visual improvement changing the power and/or focus position inside the eye of the natural crystalline lens. This process enhances accommodation.

The natural crystalline lens is removed, preferably by the standard surgical procedure of making a small incision, capsularhexis, and then phacoemulsification. During this procedure, a front portion of the capsular bag is removed by capsularhexis to then allow phacoemulsification of the natural crystalline lens. After phacoemulsification, an intraocular lens replacement is then implanted into the capsular bag through the incision. Again, existing intraocular lenses tend to provide little if any accommodation of vision of the eye. Typically, a standard intraocular lens (IOL) becomes substantially immobilized in position with a collapsed and fibrosed capsule around it so that its accommodating movement is disabled.

The artificial accommodating ocular lens (AAOL) device according to the present invention is designed and configured to replace the natural crystalline lens of the eye while also supporting accommodation of vision of the eye. Therefore, the artificial accommodating ocular lens (AAOL) according to the present invention is preferable a circular full bag lens to minimize capsular shrinkage and resist fibrosis. Specifically, the artificial accommodating ocular lens (AAOL) device according to the present invention is configured to maintain the physical anatomy of the eye, or designed to substantially maintain, recover, or even possibly enhance the accommodation of vision of the eye provided by the existing intact capsular bag zonules and cilliary muscle without the natural crystalline lens using the artificial accommodating ocular lens (AAOL) device or implant according to the present invention.

SUMMARY OF THE INVENTION

A first object of the present invention is to provide an improved artificial ocular lens (AOL) device.

A second object of the present invention is to provide an improved intraocular lens (IOL) device.

A third object of the present invention is to provide an improved artificial accommodating ocular lens (AAOL) device.

A fourth object of the present invention is to provide an accommodating artificial ocular lens (AAOL) device including a lens optic portion and a lens haptic portion.

A fifth object of the present invention is to provide an accommodating artificial ocular lens (AAOL) device including a lens optic portion connected to a pleated web lens haptic portion.

A sixth object of the present invention is to provide an accommodating artificial ocular lens (AAOL) device including a lens optic portion connected to a pleated web lens plate haptic portion.

A seventh object of the present invention is to provide an accommodating artificial ocular lens (AAOL) device including a lens optic portion connected to a pleated web lens haptic portion, the pleat folds extending in a generally radial direction.

An eighth object of the present invention is to provide an accommodating artificial ocular lens (AAOL) device including a lens optic portion connected to a flexible pleated web lens plate haptic portion provided with a plurality of radial extending pleats and folds, or undulations.

A ninth object of the present invention is to provide an accommodating artificial ocular lens (AAOL) device including a lens optic portion connected to an axial flexible lens plate haptic portion provided with a plurality of radial extending pleats and folds, or undulations.

A tenth object of the present invention is to provide an accommodating artificial ocular lens (AAOL) device including a lens optic portion connected to a thin highly flexible membrane lens plate haptic portion pleated in a radial direction.

The present invention is directed to an improved artificial ocular lens (AOL), in particular an accommodating artificial ocular lens (AAOL) device. For example, the accommodating artificial ocular lens (AAOL) device according to the present invention can be preferably implanted into the capsular bag of the eye as an improved accommodating intraocular lens (IOL), or can be implanted in a location in front of the natural crystalline lens and between the iris in the posterior chamber of the eye (e.g. phakic refractive lens, or can be implanted in the anterior chamber of the eye).

A preferred embodiment of the accommodating artificial ocular lens (AAOL) according to the present invention is an accommodating intraocular lens (AIOL or IOL) implanted in the capsular bag after removal of the natural crystalline lens, for example, by capsularhexis and phacoemulsification.

The accommodating artificial ocular lens (AAOL) according to the present invention is preferably of unitary construction, but could be multi-piece and/or multi-material, which would be unitarily bound together by methods known by those skilled in the art, and includes a lens optic portion and a lens haptic portion, preferably a lens plate haptic portion. The lens optic portion is preferably round, or can be oval, oblong, or other suitable shape for a full bag fit. Preferably, the lens haptic portion surrounds a substantial capsular contacting portion of the lens optic portion, and more preferably entirely surrounds the lens optic portion.

The plate haptic portion is preferably a pleated web or web shaped lens plate haptic portion having a plurality of pleats or pleated webs, or otherwise pleated portions connected together by pleated web folds, preferably radial extending or somewhat laterally extending pleats and folds. The plate lens haptic portion can be a pleated web configured so as to have a uniform web or haptic thickness, or more preferably is pleated in a manner so as to increase the thickness of the lens haptic portion in a lateral or radial direction outward from the center of the lens device. Specifically, the lens haptic portion is connected around or about the perimeter of the lens optic portion in a mid center plane of the lens device so that the plane of the lens optic and lens haptic approximately coincide. The pleated web folds extend radially and extend outwardly of the mid center plane of the lens device at a predetermined angle to a perimeter of the lens haptic portion. The pleated web folds preferably extend from a position of connection with the lens optic portion to the outer perimeter of the lens haptic portion. The pleated web folds can be continuous, discontinuous, or vary in shape, size and direction. This novel artificial accommodating ocular lens (AAOL) device contains a binary functional haptic that is relatively rigid in the plane of the haptic to resist capsular collapse as compared to its significantly more sensitive axially flexibility to enhance optical accommodation movements.

In a preferred embodiment, the lens device includes a lens optic portion and a lens haptic portion connected to a perimeter of the lens optic portion and surrounding the lens optic portion, the lens haptic portion being a thin flexible pleated plate member provided with a plurality of radial fold oriented in a radial direction relative to the lens optic portion with creases of the radial folds extending in a radial outward direction from the lens optic portion to an outer edge of the lens haptic portion.

The lens plate web haptic portion can have a varying thickness (e.g. thickens in an outward radial direction, thins in an outward radial or lateral direction), or alternatively, the lens plate haptic portion can be of a uniformed thickness or vary in thickness in a particular pattern (e.g. matrix, spiral, rings) to tailor or vary the flexibility of the lens plate haptic portion across or along the dimensions of the lens plate haptic portion.

The lens plate haptic portion is preferably a soft lens plate haptic portion that is highly restoratively flexible, but provides enough strength to position the lens optic portion correctly within the eye, in particular the capsular bag of the eye in a preferable accommodating location within the eye. Further, the lens plate haptic portion is substantially compliant so as to move back and forth with the tissue of the capsular bag, providing little if any resistance, while still correctly positioned within the capsular bag of the eye. Furthermore, the haptic material is rubbery and springy, and can be snappy like a surgeon's gloves so that it will return to its original position when movement forces are removed.

The artificial accommodating ocular lens (AAOL) device according to the present invention, or components or parts thereof, can be made of any biological optically transparent material such as silicone, acrylics, hydrophilics, hydrophobics, collamers, acrylates, polymethyl methacrylates, or combinations and mixtures thereof, or gel-like, with good elastic memory properties. For example, polyamide nanoparticles can be added to modify elastic and flexibility properties of the base material. The lens optic can be monofocal, bifocal, refractive, defractive, concentric, eccentric, wavefront corrected, contain special ultraviolet light inhibitors in either the ultraviolet (UV), near UV, infrared (IR), or visible light ranges, or any combination thereof (e.g. blue, clear or yellow).

In a preferred embodiment of the lens plate haptic portion, the radial extending web folds provide specific shaped or structurally tailored patterned pleated web portions. Depending on the thickness, width, shape and material characteristics the individual pleated portions can be designed to provide a particular bending arrangement of the lens device (e.g. a ogival curved arch). For example the lens plate haptic portion can increase in thickness in a radially outward direction from the point of connection with the lens optic portion towards the outer perimeter of the lens haptic portion due to the pleated web portions increasing in width. The increasing thickness of the web lens plate haptic portion tends to fill the capsular bag to simulate the thickness of the original natural crystalline lens prior to removal. The filling of the capsular by the pleated lens haptic portion tends to allow the capsular bag to operate normally, as if still containing the natural crystalline lens. Alternatively, the web pleats can be angularly radial or parallel from the centerline.

DETAILED DESCRIPTION OF PREFERRED EMBODIMENTS

Figure 1:
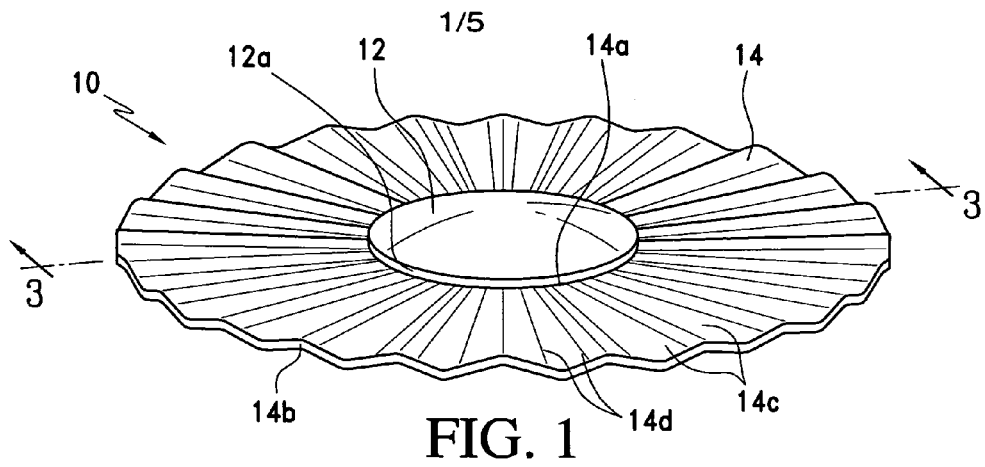
FIG. 1 is a perspective view of a first preferred embodiment of the accommodating artificial ocular lens (AAOL) device according to the present invention.
Figure 2:
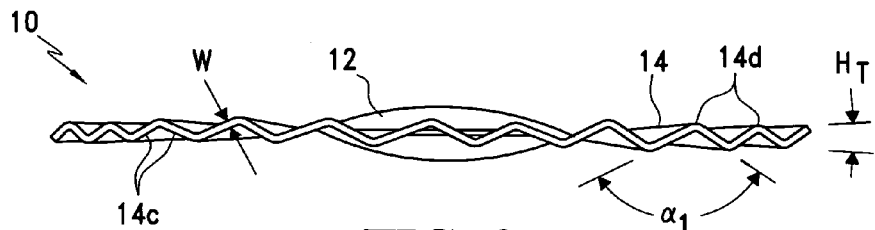
FIG. 2 is a side elevational view of the accommodating artificial ocular lens (AAOL) device shown in FIG. 1.
Figure 3:
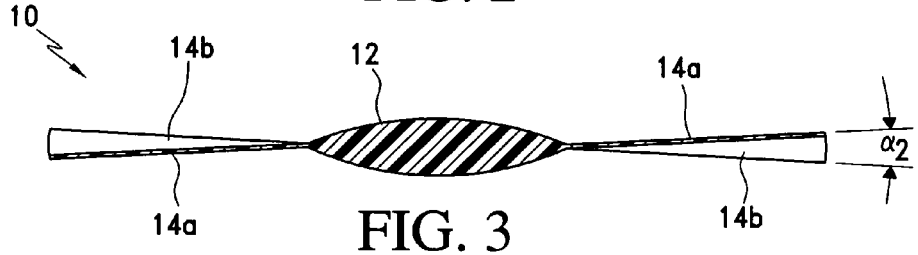
FIG. 3 is a center traverse cross-sectional view of the accommodating artificial ocular lens (AAOL) device, as indicated in FIG. 1.

A first preferred embodiment of the accommodating artificial ocular lens (AAOL) device 10 is shown in FIGS. 1-4.

The accommodating artificial ocular lens (AAOL) device 10 includes a lens optic portion 12 connected to a lens haptic portion 14. The lens optic portion 12 is shown as being circular-shaped, however, other shapes are possible (e.g. oval, oblong). The lens optic portion 12 can be configured or arranged to adjust or correct vision by adding or subtracting power (diopters) and/or adding or subtracting cylinder, and to correct for aberrations or disease of the eye. For example, the lens optic portion 12 can be monofocal, bifocal, refractive, defractive, concentric, eccentric, wavefront corrected, or combination thereof, or symmetrical or asymmetrical The lens optic portion 12 can contain special light inhibitors in the ultraviolet (UV), near UV, infrared (IR), visible light, or combination thereof.

The lens haptic portion 14 is shown as being circular-shaped, however, the lens haptic portion can have other shapes as to be discussed and described below. The lens haptic portion extends from the inner perimeter 14a to the outer perimeter 14b. The lens haptic portion 14 entirely surrounds the lens optic portion 12, and is connected to the outer perimeter of the lens optic portion 12a. The lens haptic portion 14 is a pleated web lens haptic portion, preferably a pleated lens plate haptic portion, having pleated web portions 14c and pleated web folds or creases 14d located between adjacent pleated portions 14c. The pleated portions ca be angularly even or angularly different. The outer perimeter edge 14b of the lens haptic portion is an undulating edge. The thickness of the lens haptic portion 14 increases in a radial outward direction from the connection with the lens optic portion 12 increasing in thickness to the outer perimeter edge 14b. The pleated portions 14c and pleated folds or creases 14d extend out of a center plane $C_p$ at a predetermined angle $\alpha_1$.

Figure 4B:
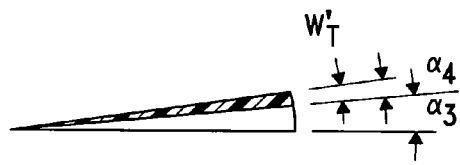
FIG. 4B is a detailed broken-away top planar view of an alternative variable web thickness pleated lens haptic portion of the accommodating artificial ocular lens (AAOL) device.
Figure 4A:
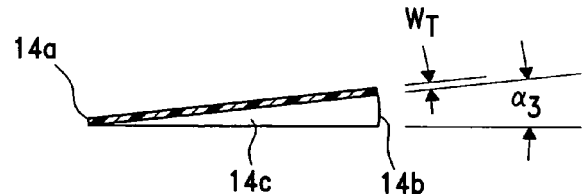
FIG. 4A is a detailed broken-away top planar view of one of a uniform thickness pleated lens haptic portion of the accommodating artificial ocular lens (AAOL) device shown in FIG. 1.
Figure 4C:
FIG. 4C is a detailed broken-away top planar view of one of a further alternative constant web width and thickness pleated lens haptic portion of the accommodating artificial ocular lens (AAOL) device.

The lens haptic portion 14 is made up of plurality of secant-shaped pleated portions 14c, as shown in FIG. 4, with constant or variable web thickness. The width of the web or pleated portion 14c increases from the inner perimeter 14a to the outer perimeter 14b, as shown in FIG. 4. The pleated portions 14c each expand in width in the radial outward direction by angle 12.

The lens haptic portion 14 is preferably a pleated lens plate haptic portion having a substantially uniform plate thickness, and being provided with a plurality of radially extending pleated web folds 14d. The pleated lens haptic portion 14, again increases in thickness in the radial outward direction from the inner perimeter 14a to the outer perimeter 14b. The increased thickness towards the outer perimeter 14b of the lens haptic portion 14 tends to fill the surrounding portion of the capsular bag of the eye when implanted into the capsular bag after removal of the natural crystalline lens.

Figure 5A:
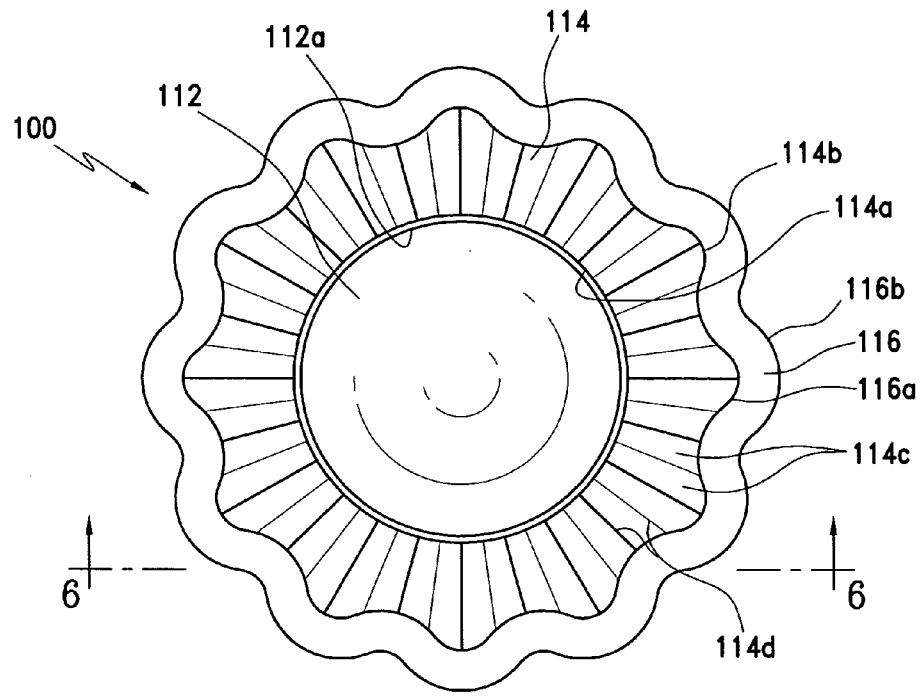
FIG. 5A is a top planar view of a second preferred embodiment of the accommodating artificial ocular lens (AAOL) device according to the present invention.
Figure 5B:
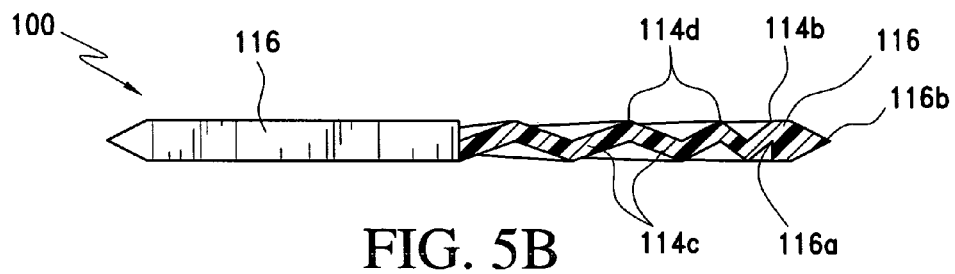
FIG. 5B is a half broken away side elevational and half center traverse cross-sectional view of the accommodating artificial ocular lens (AAOL) device, as indicated in FIG. 5A.

A second preferred embodiment of the accommodating artificial ocular lens (AAOL) device 100 according to the present invention is shown in FIGS. 5A and 5B.

The accommodating artificial ocular lens (AAOL) device 100 includes a lens optic portion 112 connected to a lens haptic portion 114. In addition, an outer perimeter ring 116 is connected to the lens haptic portion 114. Specifically, the inner perimeter 116a of the perimeter ring 116 connects to the outer perimeter 114b of the lens haptic portion 114.

The perimeter ring 116 has a serpentine shape to act as a spring, as shown in FIG. 5A. The thickness of the perimeter ring 116 can be greater than the thickness of the lens haptic portion 114, as shown in FIG. 5B. The perimeter ring 116 increases the stiffness of the outer perimeter 114b of the lens haptic portion 114.

Figure 6:
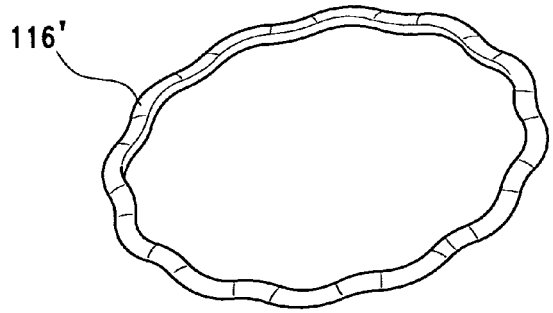
FIG. 6 is a perspective view of a separate capsular ring for use with the accommodating artificial ocular lens (AAOL) device shown in FIG. 1.

A capsular ring for use with the accommodating artificial ocular lens (AAOL) device 10 (FIG. 1) is shown in FIG. 6. The ring 116' is a separate part, and configured to function as a supplemental spring (e.g. acting like a capsular ring with or without an IOL or AAOL). The ring 116' can be used in combination with the accommodating artificial ocular lens (AAOL) device 10 shown in FIG. 1, and are implanted in combination in the capsular bag of the eye.

Various accommodating artificial ocular lens (AAOL) devices according to the present invention are shown in FIGS. 7-11.

Figure 7A:
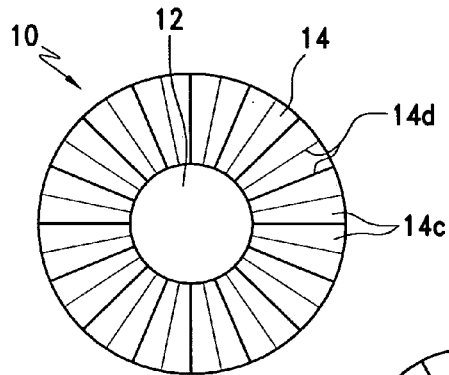
FIG. 7A is a top planar diagrammatic view of a preferred embodiment of the accommodating artificial ocular lens (AAOL) device according to the present invention, as shown in FIG. 1, having a circular-shaped configuration and a lens plate haptic portion with a radially outwardly extending pleated web lens haptic portion.

The accommodating artificial ocular lens (AAOL) device 10 shown in FIG. 7A has circular-shaped configurations, including a round lens optic portion 12 and a round lens haptic portion 14. The pleated web portions 14c are of the same size, shape, and angularity, and the pleated web folds 14d extend radially outward from the round lens optic portion 12.

Figure 7B:
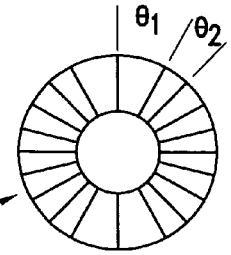
FIG. 7B is a top planar diagrammatic view of an alternative version of the preferred embodiment of the accommodating artificial ocular lens (AAOL) device according to the present invention shown in FIG. 1, having a circular-shaped configuration and a lens plate haptic portion with different size angle pleated web folds or web portions.

In the alternative embodiment shown in FIG. 7B, the pleated web portions are of different size and angularity. In another alternative embodiment shown in FIG. 7C, the pleated web portions have different size and shape (e.g. secant shape and irregular rectangular-shaped), and some of the pleated web folds extend radially outward from the round lens optic portion, and others pleated folds are both parallel and extend laterally across the round lens optic portion. In a further alternative embodiment shown in FIG. 7D, the pleated folds extend outward tangentially from the lens optic portion.

Figure 8:
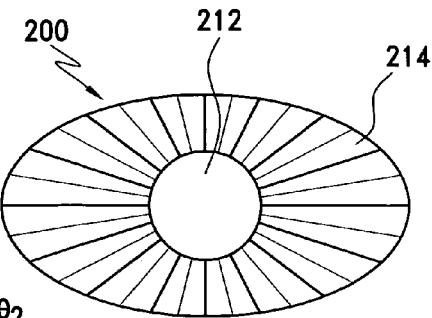
FIG. 8 is a top planar diagrammatic view of a third preferred embodiment of the accommodating artificial ocular lens (AAOL) device according to the present invention having an oval-shaped configuration.

The accommodating artificial ocular lens (AAOL) device 200 shown in FIG. 8 has a oval-shaped configuration including a circular-shaped lens optic portion 212 and a oval-shaped lens haptic portion 214.

Figure 9:
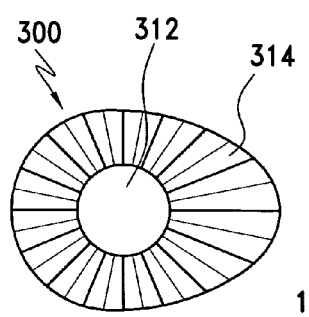
FIG. 9 is a top planar diagrammatic view of a fourth preferred embodiment of the accommodating artificial ocular lens (AAOL) device according to the present invention having an oblong-shaped configuration.
Figure 7C:
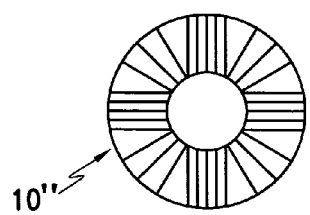
FIG. 7C is a top planar diagrammatic view of another alternative version of the preferred embodiment of the accommodating artificial ocular lens (AAOL) device according to the present invention shown in FIG. 1, having a circular-shaped configuration and a lens plate haptic portion with a combination of radially outwardly extending pleated folds and parallel pleated web folds or web portions.

The accommodating artificial ocular lens (AAOL) device 300 shown in FIG. 9 has a oblong-shaped configuration including a circular-shaped lens optic portion 312 and an oblong-shaped lens haptic portion 314.

Figure 10:
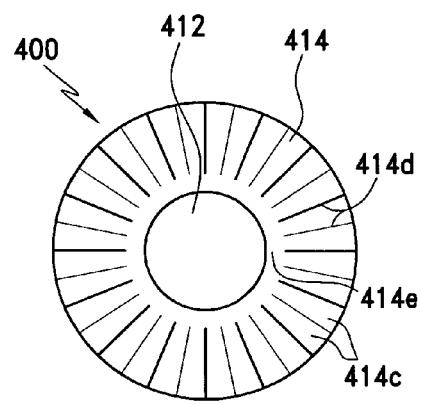
FIG. 10 is a top planar diagrammatic view of a fifth preferred embodiment of the accommodating artificial ocular lens (AAOL) device according to the present invention having a circular-shaped configuration in combination with pleated portions and pleat folds radially extending only a portion of the lens plate haptic portion.
Figure 7D:
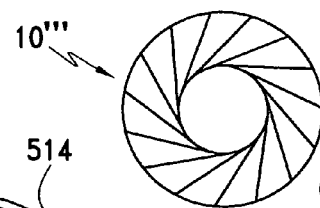
FIG. 7D is a top planar diagrammatic view of a further alternative version of the preferred embodiment of the accommodating artificial ocular lens (AAOL) device according to the present invention shown in FIG. 1, having a circular-shaped configuration and a lens plate haptic portion with tangential angulated pleated web folds or web portions.

An accommodating artificial ocular lens (AAOL) device 400 shown in FIG. 10 has a circular-shaped configuration including a round shaped lens optic portion 412 and a circular-shaped lens haptic portion 414. In this embodiment, the pleated portion 414c and web pleat folds 414d do not extend the entire lens optic portion 412 providing a flat ring-shaped haptic portion 414e.

Figure 11:
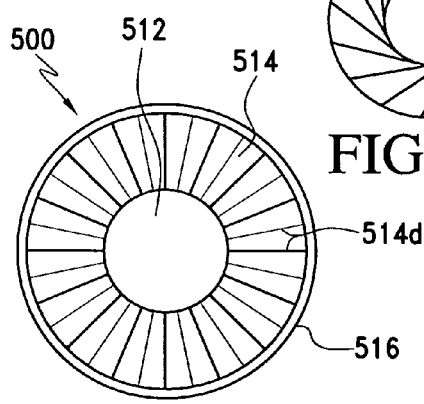
FIG. 11 is a top planar diagrammatic view of a sixth preferred embodiment of the accommodating artificial ocular lens (AAOL) device according to the present invention including an outer perimeter ring.

The accommodating artificial ocular lens (AAOL) device 500 shown in FIG. 11 has a circular-shaped configuration including a circular-shaped lens optic portion 512 and a circular-shaped lens haptic portion 514. In addition, a circular-shaped capsular ring 516 is connected to the web lens haptic portion 514.

Figure 12:
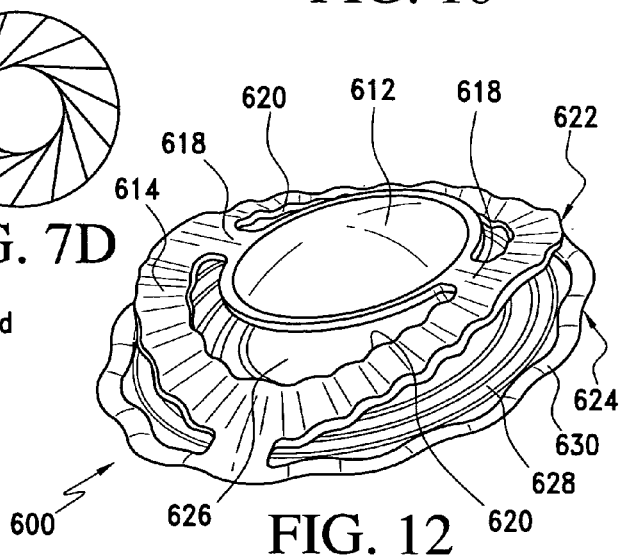
FIG. 12 is a perspective view of a seventh preferred embodiment of the accommodating artificial ocular lens (AAOL) device including a pair of lens portions connected together as shown.

A two-lens portion type accommodating artificial ocular lens (AAOL) device 600 according to the present invention is shown in FIG. 12.

The accommodating artificial ocular lens (AAOL) device 600 includes a lens optic portion 612 connected to a lens haptic portion 614 by a pair of opposed transverse arms 618. A pair of half-circle shaped slots substantially separate the lens optic portion 612 from the lens haptic portion 614. The lens haptic portion 614 is umbrella shaped, as shown in FIG. 12.

The lens optic portion 612 and the lens haptic portion 614 define a first lens portion 622 connected to a second lens portion 624. The second lens portion 624 includes a lens optic portion 626 and a lens haptic portion 628 connected to a perimeter ring 630.

Figure 14A:
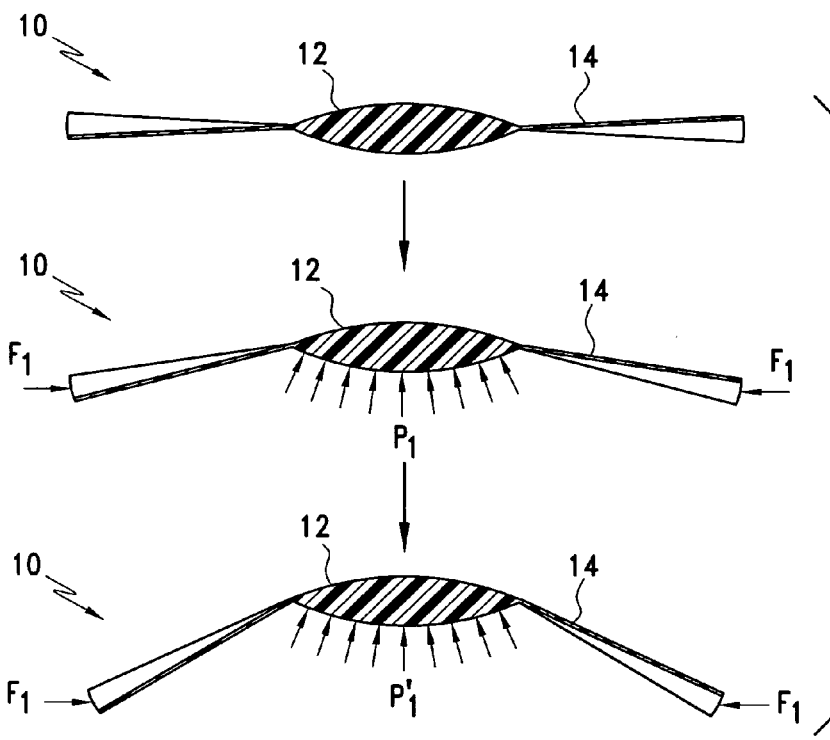
FIG. 14A is a three (3) sequence diagrammatic mid cross-sectional view showing the operation and accommodating bending movement of the accommodating artificial ocular lens (AAOL) device shown in FIG. 1.
Figure 14B:
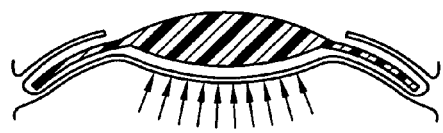
FIG. 14B is a diagrammatic mid cross-sectional view of the accommodating artificial ocular lens (AAOL) device according to the present invention implanted within the capsular bag of the eye showing the ogival bending thereof.
Figure 15:
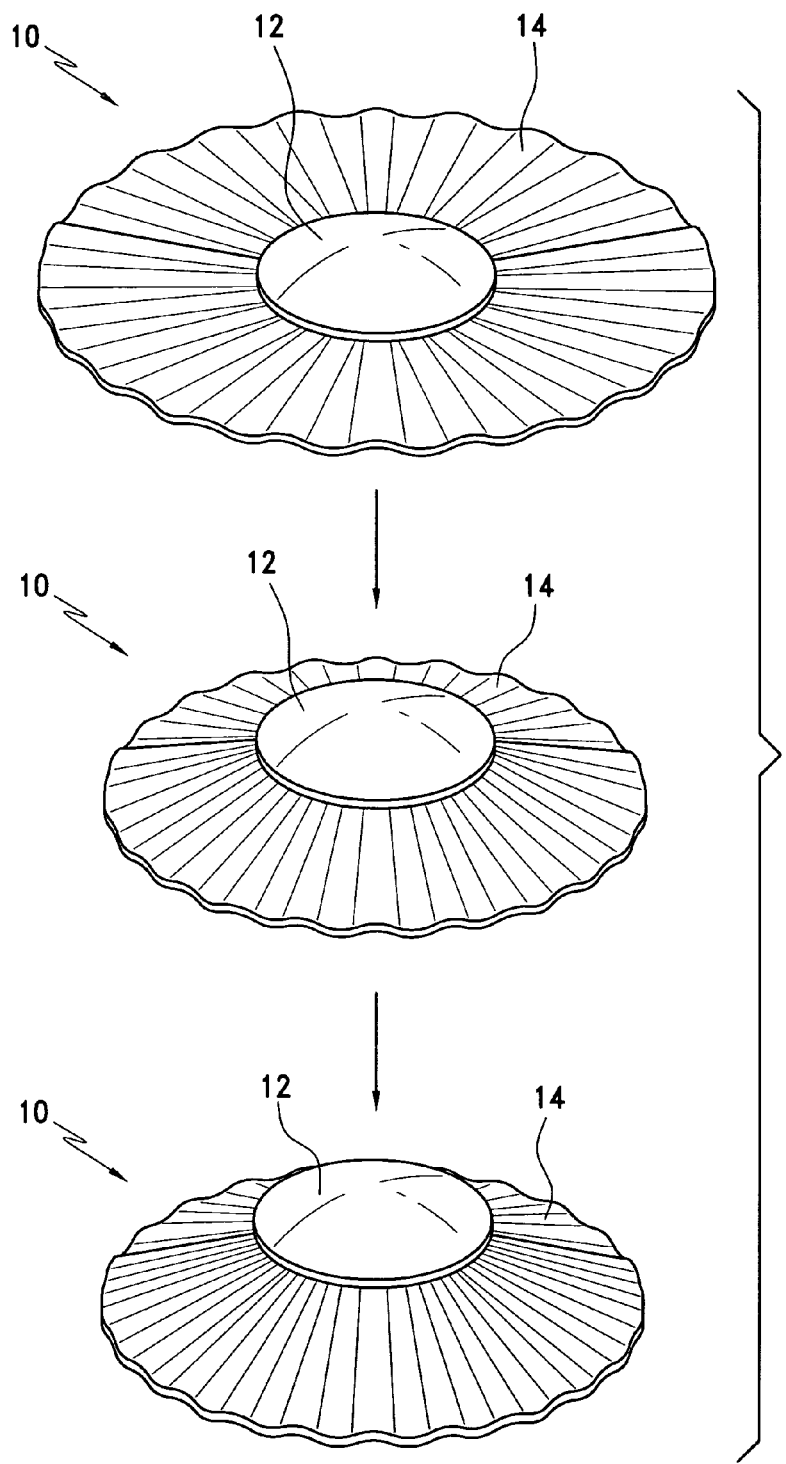
FIG. 15 is a sequence of three (3) perspective views showing the operation of the accommodating artificial ocular lens (AAOL) device shown in FIGS. 1-3.

The operation of the accommodating artificial ocular lens (AAOL) devices according to the present invention (e.g. embodiment shown in FIG. 1) is shown in FIGS. 13-15.

Figure 13A:
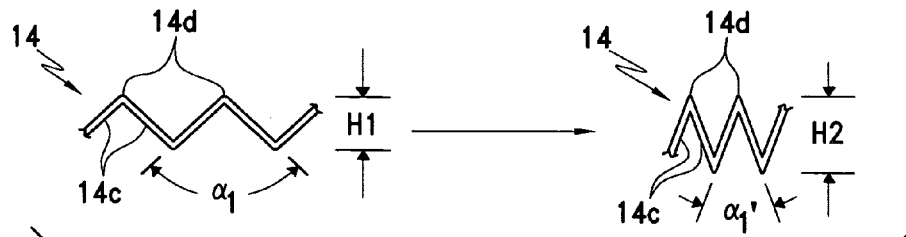
FIG. 13A is a partial broken away side elevational diagrammatic end view of a portion of the pleated web lens haptic portion illustrating the operation (i.e. expansion/compression) of the pleated web lens haptic portion of the accommodating artificial ocular lens (AAOL) device shown in FIG. 1, during accommodation.
Figure 13B:
FIG. 13B is a partial broken away side elevational diagrammatic end view of an end portion of an alternative shaped pleated lens haptic portion.
Figure 13C:
FIG. 13C is a partial broken away side elevational diagrammatic end view of an end portion of another alternative shaped pleated lens haptic portion.

The pleated web lens haptic portion is shown diagrammatically in a relaxed state on the left-hand side in FIG. 13A. When forces are applied to the lens haptic portion 14 by the eye during accommodation, the lens haptic portion 14 compresses as shown on the right hand side of FIG. 13. Specifically, the angle $\alpha_1$ steepens to angle $\alpha_1'$ when forces are applied to the lens haptic portion 14 by the capsular bag and/or are transmitted through the capsular bag of the eye to the lens device. This movement will change the projected thickness of the haptic edge for H1 to H2 (H2>H1). Alternative embodiments of the pleated web design are shown in FIG. 13B having slightly rounded folds, and FIG. 13C having very rounded folds.

As shown in FIG. 14A, the top diagram shows the accommodating artificial ocular lens (AAOL) device 10 in a resting or neutral condition. When forces $F_1$ are applied to the outer perimeter edge of the lens haptic portion 14 by the capsular bag deceasing in size as it vaults during accommodation, the lens optic portion 12 begins to vault forward within the eye. In addition, pressure $P_1$ applied to the posterior side of the capsular bag is transmitted through the capsular bag to the lens optic portion 12 to also move the lens optic portion 12 forward within the eye providing some accommodation of vision of the eye. As either the force $F_1$ or the pressure $P_1$, individually or together increases, the accommodating movement progresses, and the artificial ocular lens (AAOL) device 10 further bends as shown in the bottom diagram of FIG. 14A causing the lens optic portion 12 to significantly vault forward within the eye providing for significant refractive accommodation movement of vision of the eye. FIG. 14B shows the ogival curving bend of the web haptic 14 of the artificial ocular lens (AAOL) device 10 during accommodation within the capsular bag of the eye.

As shown in FIG. 15, a perspective view of the accommodating artificial ocular lens (AAOL) device 10 showing the accommodation operation of the lens device 10 is shown in FIG. 14. For example, the lens device 10 continuously cycles from a substantially flat neutral configuration to a partially cupped to a highly cupped configuration during accommodation movement. As accommodation movement occurs, the outside diameter of the haptic portion changes so that the circumference progressively changes in length, as the web haptic diameter changes, in a continuous dynamic manner. The neutral configuration can be a flat, slightly cupped, or significantly cupped mode depending on the particular design of the accommodating ocular lens (AAOL) device 10.

I claim:

1. An artificial accommodating lens device, said device comprising:
    a lens optic portion;
    a lens haptic portion connected to a perimeter of said lens optic portion and surrounding said lens optic portion, said lens haptic portion being a thin flexible pleated plate member provided with a plurality of radial folds oriented and extending in a radial outward direction relative to and from said lens optic portion with radial creases of said radial folds oriented and extending in a radial outward direction from said lens optic portion to an outer edge of said lens haptic portion, said radial folds having outer ends ending and located out of said center plane of said lens device, whereby said lens haptic portion positions said lens optic portion within the eye and bends relative to said lens optic portion at the perimeter connection between said lens optic portion and said lens optic portion cupping said lens device when forces are applied by an eye on said lens device to enhance accommodation of vision of the eye.

2. An artificial accommodating lens device, said lens device comprising:
   a lens optic portion; and
   a lens haptic portion connected to said lens optic portion and at least partially surrounding said lens optic portion, said lens haptic portion being a thin flexible pleated plate member provided with a plurality of radial folds oriented and extending is a radial direction relative to said lens optic portion with radial creases of said radial folds oriented and extending in a radial outward direction, whereby said lens haptic portion centers said lens device within the eye and bends relative to said lens optic portion cupping said lens device when forces are applied by an eye on said lens device to provide accommodative movement to enhance vision of the eye.

3. The lens device according to claim 1, wherein said lens haptic portion is defined by a plurality of pleated secant-shaped web portions connected together, said pleated web portions increasing in width from an inner radial position to an outward radial position of said lens haptic portion.

4. The lens device according to claim 1, wherein said lens haptic comprises pleated web portions, wherein adjacent said pleated web portions are joined together along said pleated folds.

5. The lens device according to claim 1, wherein said radial folds extend out of the center plane of said lens device at a predetermined angle.

6. The lens device according to claim 4, wherein said radial folds extend out of the center of said lens device at a predetermined angle.

7. The lens device according to claim 1, wherein said lens optic portion is round-shaped.

8. The lens device according to claim 1, wherein said lens haptic portion is round-shaped.

9. The lens device according to claim 7, wherein said lens haptic portion is round-shaped.

10. The lens device according to claim 1, wherein said lens haptic portion is oval-shaped.

11. The lens device according to claim 1, wherein said lens haptic portion is oblong-shaped.

12. The lens device according to claim 1, further comprising a ring portion connected to said lens haptic portion.

13. The lens device according to claim 12, wherein said ring is connected to a perimeter of said lens optic portion.

14. The lens device according to claim 2, wherein said radial folds extend from an outer perimeter of said lens optic portion to an outer perimeter of said lens haptic portion.

15. The lens device according to claim 2, wherein said pleated folds extend from a predetermined distance from a perimeter of said lens optic portion to an outer perimeter of said lens haptic portion.

16. The lens device according to claim 2, wherein said pleated folds extend from an outer perimeter of said lens portion to a predetermined distance from an outer perimeter of said lens haptic portion.

17. The lens device according to claim 1, wherein a plurality of said pleated folds are slit to provide added flexibility to said lens haptic portion.

18. The lens device according to claim 1, further comprising a second lens optic portion connected to a second lens haptic portion, said first lens haptic portion being connected to said lens haptic portion, and said first optic portion optically cooperating with said second optic portion to provide accommodation of vision of the eye.

19. The lens device according to claim 1, wherein said lens haptic portion further comprises pleated web portions, wherein said pleated web portions are secant-shaped, and have said secant-shaped web portions comprise an equal angle.

20. The lens device according to claim 1, wherein said lens haptic portion further comprises pleated web portions connected together by said radial folds, wherein said pleated web portions are secant-shaped, and said secant-shaped web portions comprise an equal angle.

21. The lens device according to claim 1, wherein said lens haptic portion further comprises pleated web portions, wherein said pleated web portions of said lens haptic portion extend radially outwardly from said lens optic portion.

22. The lens device according to claim 1, wherein at least some of said pleated folds are parallel to each other.

23. The lens device according to claim 1, wherein a perimeter of said lens haptic portion changes in length as the lens device cups during accommodative movement.

24. The lens device according to claim 1, wherein an angle between adjacent pleated portions changes as a result of cupping of said lens haptic portion during accommodative movement.

25. The lens device according to claim 1, wherein an angle between adjacent pleated portions changes and the perimeter of said lens haptic portion changes as the lens device cups during accommodative movement.

26. The lens device according to claim 1, wherein said lens device cups during accommodative movement, and said cupping is of an ogival shape.

27. An artificial accommodating lens device, said device comprising:
   a lens optic portion; and
   a lens haptic portion connected to said lens optic portion, said lens haptic portion being a thin flexible pleated plate member provided with a plurality of radial folds having radial creases oriented and extending in a radial outward direction relative to and from said lens optic portion, whereby said lens device cups when forces are applied by an eye on said lens device to enhance accommodation of vision of the eye.

* * * * *